(12) United States Patent
Brada et al.

(10) Patent No.: US 7,809,102 B2
(45) Date of Patent: Oct. 5, 2010

(54) METHOD AND APPARATUS FOR POSITIONING A SUBJECT IN A CT SCANNER

(75) Inventors: Rafael Brada, Hod Hasharon (IL); Ehud Dafni, Caesarea (IL)

(73) Assignee: Arineta Ltd., Caesarea (IL)

(*) Notice: Subject to any disclaimer, the term of this patent is extended or adjusted under 35 U.S.C. 154(b) by 173 days.

(21) Appl. No.: 12/120,841

(22) Filed: May 15, 2008

(65) Prior Publication Data

US 2009/0285355 A1    Nov. 19, 2009

(51) Int. Cl.
*A61B 6/00* (2006.01)
*A61B 6/02* (2006.01)
(52) U.S. Cl. .......................... 378/20; 378/41
(58) Field of Classification Search ............. 378/4, 378/8, 9, 41–46
See application file for complete search history.

(56) References Cited

U.S. PATENT DOCUMENTS

| | | | |
|---|---|---|---|
| 4,712,226 A | 12/1987 | Horbaschek | |
| 4,819,255 A | 4/1989 | Sato | |
| 5,233,639 A | 8/1993 | Marks | |
| 5,661,772 A | 8/1997 | Bar et al. | |
| 5,751,788 A | 5/1998 | Khutoryansky et al. | |
| 5,995,581 A | 11/1999 | Ozaki | |
| 6,181,768 B1 | 1/2001 | Berliner | |
| 6,198,790 B1 | 3/2001 | Pflaum | |
| 6,269,501 B1 | 8/2001 | Li et al. | |
| 6,302,579 B1 | 10/2001 | Meyer et al. | |
| 6,317,481 B1 | 11/2001 | Berestov | |
| 6,862,364 B1 * | 3/2005 | Berestov ................... 382/132 |
| 6,914,959 B2 * | 7/2005 | Bailey et al. ................ 378/65 |
| 7,031,425 B2 * | 4/2006 | Hsieh et al. .................. 378/5 |
| 7,065,179 B2 | 6/2006 | Block et al. | |
| 7,113,569 B2 | 9/2006 | Okumura et al. | |
| 7,164,745 B2 | 1/2007 | Tsuyuki | |
| 7,313,213 B1 | 12/2007 | Hsieh et al. | |
| 7,313,215 B2 | 12/2007 | Hsieh et al. | |
| 7,333,587 B2 | 2/2008 | De Man et al. | |
| 2004/0001571 A1 | 1/2004 | Jahrling | |

(Continued)

FOREIGN PATENT DOCUMENTS

EP    0480035    4/1992

(Continued)

OTHER PUBLICATIONS

"Focal-Spot Separation in Stereoscopic Magification Radiography", Takashai et al., from Radiation Physics: Radiology 140: 227-229, Jul. 1981.

(Continued)

*Primary Examiner*—Irakli Kiknadze
(74) *Attorney, Agent, or Firm*—Eitan Mehulal Law Group

(57) ABSTRACT

An apparatus and method for optimally positioning a region of interest of a subject for imaging by a CT scanner. The scanner provides a source of one or more X-ray beams, at least one of which is used for acquiring a CT image of the subject, a movable support for the subject, and a controller that controls the X-ray source. To position the region of interest of the subject, the controller operates to illuminate the subject with X-rays to acquire stereo image data for the region of interest and controls the position of the support responsive to the stereo image data.

27 Claims, 6 Drawing Sheets

U.S. PATENT DOCUMENTS

2005/0053192 A1 3/2005 Sukovic et al.
2006/0285633 A1 12/2006 Sukovic et al.
2009/0238334 A1* 9/2009 Brahme et al. ................ 378/41

FOREIGN PATENT DOCUMENTS

EP 1887937 2/2008
JP 07-222738 8/1995

OTHER PUBLICATIONS

"Stereoscopic Magnification Angiography using a Twin Focal-Spot X-Ray Tube" Takahashi et al., from Radiation Physics: Radiology 142: 791-792, Mar. 1982.

"Machine Precision Assessment for 3D/2B Digital Subtracted Angiography Images Registration", E. Kerrien et al., Proceedings of SPIE Medical Imaging 1998, K. Hanson Ed, vol. 3338, pp. 39-49, Sand Diego, Feb. 23-26, 1998.

"Biplane Stereoscopic Magnification Cerebral Angiography", J. Kleefeld et al., Radiology 1987; 165: 576-577.

"Three-Dimensional Cardiac Imaging and Catheter Tracking in Atrial Fibrillation Ablation", Jaswal et al., Indian Heart J. 2007; 59(3): 1-9.

"Introduction to Technology for LCD Components Electronic Components", Sharp Corporation, 2006.

"Integrated Electroanatomic Mapping with Three-Dimensional Computed Tomographic Images for Real-Time guided Ablations", Circulation, Journal of the American Heart Association, 2006; 113: 186-194.

PCT/IL2007/000461, Filed on Apr. 10, 2007 and entitled: "X-Ray Tube", applicant Arineta Ltd.

PCT/IL2007/000462, filed on Apr. 10, 2007 and entitled: "Cone Beam CT", applicant: Arineta Ltd.

* cited by examiner

METHOD AND APPARATUS FOR POSITIONING A SUBJECT IN A CT SCANNER

FIELD OF THE INVENTION

The present invention relates to computed tomography (CT) X-ray imaging and more particularly to a method and apparatus for positioning a subject relative to a CT scanner.

BACKGROUND OF THE INVENTION

In CT imaging, cross sectional axial images or slices of a volume of interest (VOI), for example, of a patient's body or, more generally, of an object under inspection, are created by computer processing of X-ray attenuation data acquired at multiple view angles around an axis of rotation.

FIG. 1 is a schematic illustration of some basic features of a typical CT scanner 100 used for medical imaging. CT scanner 100 comprises a support rotor 102 mounted on a gantry (not shown) that carries an X-ray source 104 and a detector array 106, the latter being comprised of a plurality of rows 108 and columns 110 of closely spaced X-ray detector elements 112. Support rotor 102 is arranged for rotation in a direction indicated by an arrow 116 around a rotational axis coinciding with the Z-axis 134 of a coordinate system indicated by coordinate icon 114. It should be noted that coordinate system 114 rotates with rotor 102 so the Y axis remains pointing from the center of rotation to the X ray source 104 while the system is rotating.

A movable platform 118 is arranged to transport a patient 120 (or, more generally, an object being inspected) along the scanner Z-axis as indicated by arrow 122. A system controller 124 controls the operation of rotor 102, X-ray source 104, platform 118, as well as an image processor 126 connected to an output of detector array 106, and a display and storage unit 128.

One mode of operation is sometimes referred to as "step and shoot". In this mode, platform 118 is held at a fixed axial position, and CT scanner 100 generates an X-ray beam 130 that emanates from a focal point 131 at source 104, and impinges on the detector elements 112 after passing through the patient's body. The X-ray beam may be fan-shaped, or as illustrated in FIG. 1, cone-shaped. Attenuation data from all the detector elements 112 is gathered for a succession of angular positions (or view angles), typically in the range of about 180 to about 360 degrees, as rotor 102 carries source 104 and detector array 106 around the subject.

The data collected from all the detector elements for all the viewing angles at a fixed axial position, generally referred to as projections, are computer-processed by image processor 126 to reconstruct one or more two-dimensional slice images. The slice images are displayed and stored by display and storage unit 128, which may include a computer monitor, or of any other desired and suitable display type, and a suitable data storage unit. In the case of a cone beam, a three-dimensional image may be created from the reconstructed axial slices. Combining the projection data from multiple axial positions obtained by moving platform 118 in steps allows creation of a larger three-dimensional image or scanned volume.

Alternatively, a CT scanner can be operated in a "spiral scan" mode in which the X-ray source and detector array rotate continuously, and the platform moves continuously along the axis of rotation.

A consideration in the use of CT for medical imaging is minimizing exposure to the radiation, both in and outside a VOI. Therefore, it is desired to position the patient optimally in the Z direction so the scanner covers the VOI. For good image quality, the scanner field of view (FOV) as defined below is desirably made large enough to encompass the portions of the subject radially extending outside of the precise VOI However, it is possible to scan the peripheral parts of the FOV with reduced dose (by using a butterfly or other filter) and/or reduced resolution. Further, CT scanners have a higher spatial resolution in the region close to the center of rotation. Consequently, for the VOI to have optimal image quality, it will generally be advantageous for the VOI to be located substantially at the center of the scanned volume. Further, with such a configuration it is possible to reconstruct the full images only within a limited volume around the VOI within the scan FOV whereas the rest of the data is used for image correction only.

In general, achieving a desired scan volume involves controlling the FOV of the scanner and selecting the number of axial positions at which projections are obtained. The FOV depends on the geometry of the scanner, and the collimation of the X-ray beam. For example, for an X-ray beam 130 that emanates symmetrically from X-ray source 104 relative to Z-axis 134, the size of the FOV is defined by a largest circle in a plane perpendicular to the z-axis (XY plane) that has its center on the rotation-axis and for which trajectories of X-rays from the X-ray source that are detectable by the azimuthal edges of the detector array are substantially tangent to the circle. This is indicated in FIG. 1 by dashed-line circle 132 having a radius $R_1$ centered on the scanner Z-axis 134 for a symmetrically located detector array.

For a given cone beam geometry we define a volume field of view (VFOV) to be the volume that can be reconstructed from a circular scan, as depicted in FIG. 3B for a dual source scanner as explained hereinbelow.

For beams that are asymmetric relative the Y-axis, for a 360-degree rotation or larger scan, the larger angle relative to the radius determines the FOV. For scans of less than 360 degrees, the smaller angle determines the FOV.

Another known way to achieve a desired scan volume is to employ multiple spaced X-ray beams, either from multiple X-ray sources, or from a single source having multiple focal spots or X-ray beam emanation points. Numerous examples of X-ray emitters having multiple focal spots are known in the art, for example, U.S. Published Patent Application 2006/0285633, published Dec. 21, 2006 and entitled MULTIPLE SOURCE BEAN CT SCANNER (the '633 Patent Application), and U.S. Pat. No. 7,333,587 Issued Feb. 19, 2008, and entitled METHOD AND SYSTEM FOR IMAGING USING MULTIPLE OFFSET X-RAY EMISSION POINTS (the '587 Patent), the disclosures of which are incorporated by reference herein. The multiple X-ray beams may emanate from points spaced along the path of rotation, as in the case of emanation points 206a and 206b in FIG. 2 as discussed in detail below. Alternatively the emanation points may be spaced along a line parallel to the axis of rotation, as in the case of focal spots 306a and 306b in FIGS. 3A-3C. The spaced beams may be switched on and off at a high frequency as the rotor 102 rotates around the Z-axis to provide alternating partial projections that are computer-processed to provide a volumetric image.

According to conventional practice, a preliminary planar scan (with the rotor placed at fixed angle) is used to plan the positioning of the axial CT slices. In fan beam scanners, where the detector has a limited coverage in the Z direction, the patient is made to move in the Z direction during scan and the CT scanner is used substantially as a line scanner. In cone beam scanners having a sufficient number of detectors rows, the planar scan can be done by a single shot on a static patient or by a step and shoot procedure that comprises a small number of steps, depending on the area to be covered. For the single shot or step and shoot planar scan, the CT scanner is used as a digital radiography device. For planning CT scans of the body, "planar scan" radiographic images are typically acquired with the X ray source at 0 degrees or 180 degrees. For planning CT scans of the head, "planar scan" radiographic images are typically acquired with the X ray source at 90 degrees or 270 degrees.

To align the patient in left/right and up/down directions, two positioning scans would have to be performed (i.e., a first scan at 0 degrees for horizontal alignment and, and a second scan at 90 degrees for vertical alignment). This can be time consuming and an inconvenience for both the technician operating the scanner and the patient.

Typically, horizontal positioning (in/out along the Z-axis) is performed by computer control. Vertical alignment is done, if at all, by manual adjustment based on external laser markers projected on the patient. Motorized lateral (left/right) alignment capability is not provided in CT scanners available commercially; the patient supports do not even provide a degree of freedom for left/right positioning. Nevertheless left/right positioning is desirable for cardiac imaging since the heart is typically shifted to the left and a minor shift of the patient to the right is generally needed for proper alignment. This shift is sometimes achieved by sliding the patient sideways on the patient support.

It is also known that image resolution is highest and image artifacts are minimized near the center of the FOV. Being able to center the VOI in all three dimensions is advantageous for this reason as well.

SUMMARY OF THE INVENTION

According to some embodiments of the present invention, stereo X-ray image data are used for aligning a VOI of a subject relative to the VFOV of a CT scanner.

According to some embodiments of the invention, in CT scanners having a single X-ray beam, a first radiography image is generated with the source at a fixed angle. The patient platform is then moved in a direction transverse to the X-Ray emission direction by a small distance and a second image is generated. The distance of movement between the two images is small enough that there is a good overlap between the images. The image data so acquired is used for alignment of the subject.

According to some embodiments of the present invention, in CT scanners having the capability for generating multiple spaced X-ray beams, two beams are used to acquire the stereo image data.

According to some embodiments of the invention, the stereo image data are obtained in a single operation without having to move the subject and then repeat the process.

According to some embodiments of the invention, the stereo positioning images are obtained in a single operation without having to move the source and then repeat the process.

According to some embodiments of the invention, in a CT scanner arranged to provide two spaced X-ray beams, the two beams are used in a stereo projection mode to provide planar stereo images for use in aligning a VOI of a subject in one, two, or three dimensions relative to the VFOV, of the scanner.

The term "fluoroscopy" or "fluoroscopic" is used here in its conventional sense to refer to the generation of planar X-ray images in real time using relatively low beam power and having relatively low resolution (compared, for example, to a CT scan). The term "stereo fluoroscopy" or "stereo fluoroscopic" refers to generation of displaced-viewpoint planar X-ray images which may be displayed for viewing each by one eye only to yield a three-dimensional (3D) image, or computer processed to extract 3D information.

According to some embodiments of the invention, in a CT scanner arranged to provide multiple spaced X-ray sources in which multiple (typically, two) X-ray beams are used to provide stereo images for positioning a subject relative to the scanner VFOV, one or more of the beams are used to acquire the data for creating the CT image.

According to some embodiments, for medical imaging, rapid electronic switching between beams, allows heart and breathing motion to be substantially frozen, thereby improving the quality of the positioning images.

According to some embodiments, for medical imaging, an ECG signal is employed for triggering the stereo image acquisition at a desired phase of the cardiac cycle. Optionally, an ECG signal may also be employed for identifying the phase of the cardiac cycle at which the positioning images were taken.

According to some embodiments, for medical imaging, a raw ECG signal or a breath monitor may be employed to select the breath phase when triggering the stereo image acquisition. Optionally, the raw ECG signal or breath monitor may be employed to identify the breath phase at which the positioning images were taken. Further optionally, the timing of the positioning image may be arranged to coincide with the same breath phase at which the CT scan will be performed.

According to some embodiments of the invention, stereo positioning images obtained as described above may be used in a manual mode, an operator-assisted semi-automatic mode, or a fully automatic mode, to position the subject at the desired location relative to the VFOV.

Therefore, according to a first aspect of this invention, a CT scanner for imaging a VOI of a subject is provided which comprises a source of one or more X-ray beams, wherein the source is adapted to provide at least one beam for acquiring a CT image of the body, a support that supports the subject, and a controller that controls the X-ray source to illuminate the region of interest with X-rays to acquire stereo image data for the region of interest and controls the position of the support responsive to the stereo image data.

Optionally, a CT scanner according to the first aspect of the invention comprises at least one detector that receives X-ray beams provided by the X-ray source and defines with the X-ray beams a field of view of the CT scanner. Optionally, in such a CT scanner, the controller controls the support to center the region of interest in the field of view.

Optionally, in a CT scanner according to the first aspect of the invention, multiple X-ray beams emanate from multiple X-ray focal spots located in a same X-ray tube.

Optionally, in a CT scanner according to the first aspect of the invention, multiple X-ray beams emanate from separate X-ray tubes.

Optionally, in a CT scanner according to the first aspect of the invention, X-rays emanate from multiple emission points that are spaced in a direction of rotation of the emission points around the subject.

Optionally, in a CT scanner according to the first aspect of the invention, X-ray beams emanate from multiple X-ray focal spots or separate X-ray sources spaced transversely to a direction of rotation of the X-ray beams around the subject on a line parallel to an axis of rotation of the X-ray beams.

Optionally, according to the first aspect of the invention, the stereo image data represent a real time fluoroscopic stereoscopic image.

Optionally, according to the first aspect of the invention, the stereo image data are comprised of two images derived from X-rays emitted from a single X-ray emission point, a first image being obtained with the subject platform at a first location, and the second image being obtained after the subject platform has been moved a small distance in a direction transverse to the X-Ray emission direction of the scanner such that the resulting images overlap.

Optionally, according to the first aspect of the invention, the stereo image data represent two separate images and the controller is operative to apply an image processing algorithm to the separate images to control the position of the support.

Optionally, according to the first aspect of the invention, the controller is operative to provide visual data to an operator for use by the operator in controlling the position of the support in one or more dimensions.

Optionally, according to the first aspect of the invention, the controller is operative to control the position of the support in a fully automatic mode, or in a semi-automatic mode, responsive to input data from an operator.

According to a second aspect of the invention, there is provided a method of operating a CT scanner to acquire a CT image of a region of interest of a subject, the scanner being operable to generate X-rays from a source having at least one emission point and having a detector array that cooperates with the X-ray source to define a field of view for the scanner, wherein the method comprises illuminating a region of the subject encompassing the region of interest using X-rays emitted from the X-ray source, generating stereo image data for at least part of the illuminated region responsive to an output from the detector array, positioning the region of interest at a desired location relative to the scanner in response to the stereo image data, and generating a CT image of the region of interest positioned at the desired location.

Optionally, according to the second aspect of the invention, the desired location at which the region of interest is positioned is substantially centered along a rotational axis of the scanner.

Optionally, according to the second aspect of the invention, the region of interest is a heart of a patient, and the stereo image data is generated responsive to a selected phase of a cardiac cycle of the patient or a selected breath phase of the patient.

Optionally, according to the second aspect of the invention, the phase of the cardiac cycle is determined from an ECG signal.

Optionally, according to the second aspect of the invention, the breath phase of the patient is determined from a breath monitor signal.

Optionally, according to the second aspect of the invention, the stereo image data is generated by alternatingly illuminating the region of the subject encompassing the region of interest with X-rays emitted from two emission points which are switched on an off during multiple repetition cycles.

Optionally, according to the second aspect of the invention, the region of interest is a heart of a patient, and the method further includes the steps of using an ECG signal to identify a phase of the cardiac cycle at which the stereo image data were generated; and generating the CT image using the identified phase of the cardiac cycle for timing.

Optionally, according to the second aspect of the invention, the region of interest is a heart of a patient, and the method further includes the steps of selecting a breath phase at which the stereo image data will be generated using a signal from an ECG or from a breath monitor; and generating the CT image of the region of interest at the same breath phase for which the stereo image data were generated.

Optionally, according to the second aspect of the invention, the step of generating the stereo image data comprises obtaining two images from X-rays emitted from a single X-ray emission point, a first image being obtained with the subject platform at a first location, and the second image being obtained after the subject platform has been moved a small distance in a direction transverse to the X-Ray emission direction such that the resulting images overlap.

Optionally, according to the second aspect of the invention, the step of generating the stereo image data comprises illuminating the region of the subject encompassing the region of interest with multiple repetition cycles of X-rays from a first and a second X-ray emission point, each repetition cycle being comprised of a first period during which X-rays are emitted only from the first emission point and a second period of approximately the same duration as the first period during which X-rays are emitted only from the second emission point, wherein the combined duration of the first and second periods is less than the total duration of the repetition period.

Optionally, according to the second aspect of the invention as described in the preceding sentence, the region of interest is a heart of a patient, and the repetition period is based on a cardiac cycle as indicated by an ECG output signal.

According to a third aspect of the invention, a CT scanner for imaging a region of interest of a subject is provided, in which an X-ray source is operable to provide first and second X-ray beams, a platform that supports the subject, a detector array positioned to intercept X-rays emitted by the X-ray source, and a controller that controls the X-ray source to generate the first and second X-ray beams to illuminate the subject, and is responsive to an output from the detector array when illuminated by the first and second X-ray beams to generate stereo image data for the subject, the controller being operable in a positioning mode responsive to the stereo image data to position the platform at a desired location for acquiring a CT image of the region of interest, and operable in a scanning mode to illuminate the region of interest with an X-ray beam from the X-ray source, and responsive to an output of the detector array when operated in the scanning mode to generate a CT image of the region of interest.

Optionally, according to the third aspect of the invention, the controller is operative in the scanning mode responsive to the stereo image data to control the X-ray source such that the CT image of the region of interest is acquired without exposing portions of the body outside the region of interest to substantial radiation.

Optionally, according to the third aspect of the invention, the first and second X-ray beams emanate from first and second X-ray focal spots located in a single X-ray tube.

Optionally, according to the third aspect of the invention, the X-ray beams emanate from separate X-ray tubes.

Optionally, according to the third aspect of the invention, the X-ray beams emanate from points that are spaced in a direction of rotation of the X-ray beams around the subject.

Optionally, according to the third aspect of the invention, the X-ray beams emanate from points that are spaced transversely to a direction of rotation of the X-ray beams around the subject on a line parallel to an axis of rotation of the X-ray beams.

Optionally, according to the third aspect of the invention, the controller is operative to provide visual data to an operator for use by the operator in controlling the position of the platform in one or more dimensions.

Optionally, according to the third aspect of the invention, the controller is operative to control the position of the platform in a fully automatic mode, or in a semi-automatic mode, responsive to input data from an operator.

BRIEF DESCRIPTION OF THE DRAWINGS

An illustrative embodiment of the invention is described below with reference to the attached drawings. Other embodiments and additional aspects of the invention will be apparent to persons skilled in the art from the description and drawings, in which.

Figure 1:
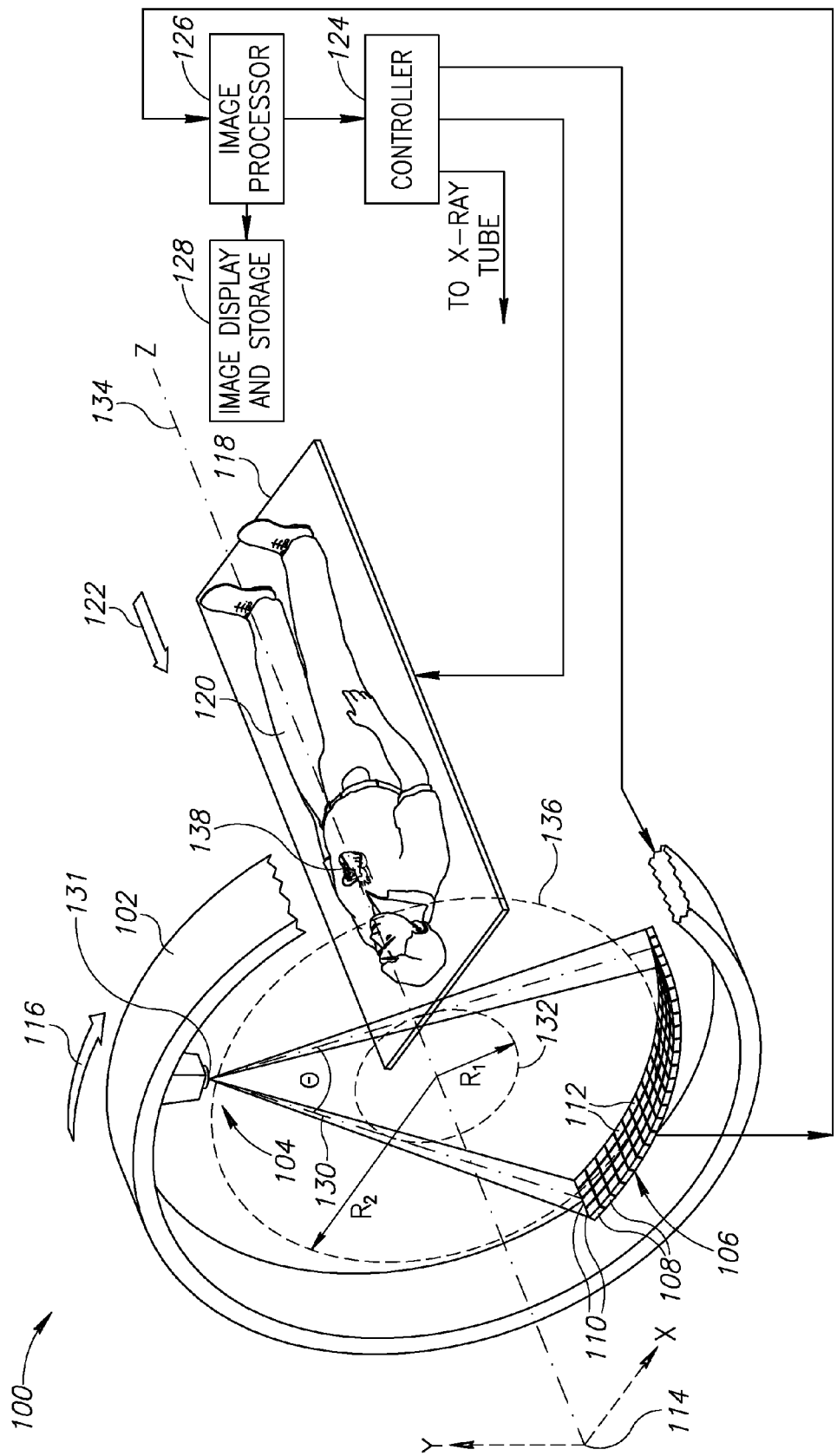
FIG. 1 is a pictorial perspective view showing certain basic features of a conventional CT scanner.

In the drawing figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale.

DETAILED DESCRIPTION OF THE INVENTION

Figure 2:
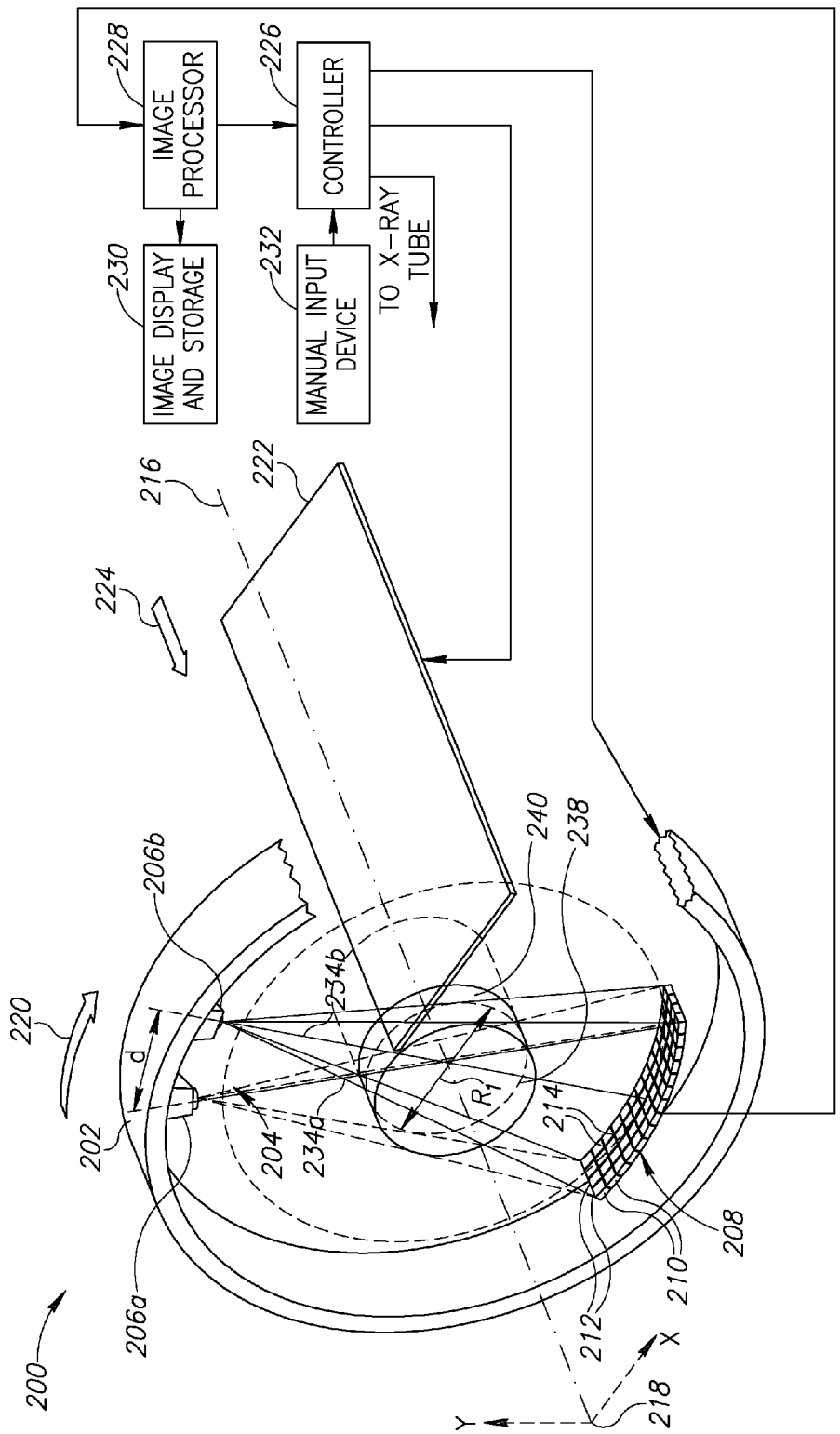
FIG. 2 is a pictorial perspective view similar to FIG. 1 showing basic features of a CT scanner according to an embodiment of the present invention.

According to an embodiment of the invention, accurate positioning of a VOI of a subject in the VFOV of a CT scanner may be achieved with an arrangement as illustrated in FIG. 2. By way of a non-limiting example, the invention will be illustrated and described in the context of positioning a patient for cardiac imaging.

Referring to FIG. 2, CT unit 200 comprises a rotating support 202 on which is carried a dual beam X-ray source 204, shown schematically as being comprised of separate X-ray emitters 206a and 206b separated by a distance d in the direction of rotation 220 of rotor 202. A detector array 208 comprised of a plurality of rows 210 and columns 212 of X-ray detector elements 214 is supported by rotor 202 and positioned to intercept X-ray beams 234a and 234b provided by source 204 after the beams pass through a subject on support platform 222. Optionally, detector array 208 may be configured to provide greater resolution in its central portion than in the outer rows and columns, as in European Published Patent Application No. EP 1887937A2, published Feb. 20, 2008, entitled GRADED RESOLUTION FIELD OF VIEW CT SCANNER.

Also, optionally, emitters 206a and 206b may be separate X-ray sources contained in a single housing, or may be provided by multiple focal spots in a single X-ray tube, as in the '633 Patent Application and '587 Patent referred to above.

Also, while X-ray source 204 is shown providing X-ray beams emanating from two emission points, more than two emission points may be provided if desired.

As shown in FIG. 2, X-ray beams 234a and 234b are cone beams. This results in a cylindrical VFOV 240 centered on rotation (Z) axis 216. For symmetrical beams, VFOV 240 extends along axis 216 equal distances on opposite sides of a central X-Y plane of the scanner, indicated by broken line circle 238 (and corresponding to circle 132 in FIG. 1).

Support rotor 202 is arranged for rotation around the Z-axis 216 of the scanner (see coordinate icon 218) in the direction of arrow 220. Patient transport platform 222 is arranged for travel along the scanner Z-axis as indicated by arrow 224, and also for incremental lateral and vertical positioning adjustment. A system controller 226 controls the operation of rotor 202, X-ray source 204, platform 222, as well as an image processor 228 connected to the output of detector array 208, and a display and storage unit 230, which may be like display and storage unit 128 (see FIG. 1).

Additionally, there is provided a manual input device 232, which may include one or more of a keyboard, mouse, joystick, etc., connected to controller 226 for manually inputting data as described below.

Figure 3A:
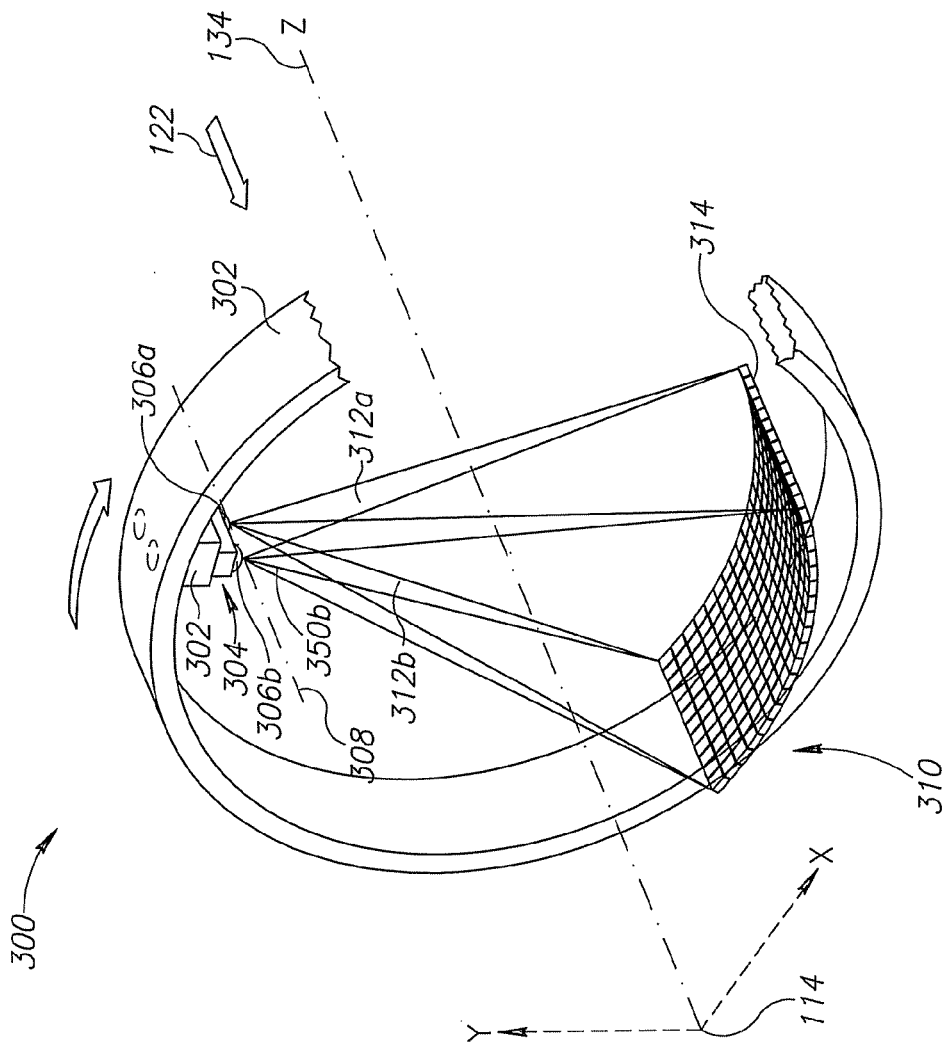
FIG. 3A is a pictorial perspective view showing basic features of an embodiment which is a variation of the embodiment of FIG. 2.
Figure 3B:
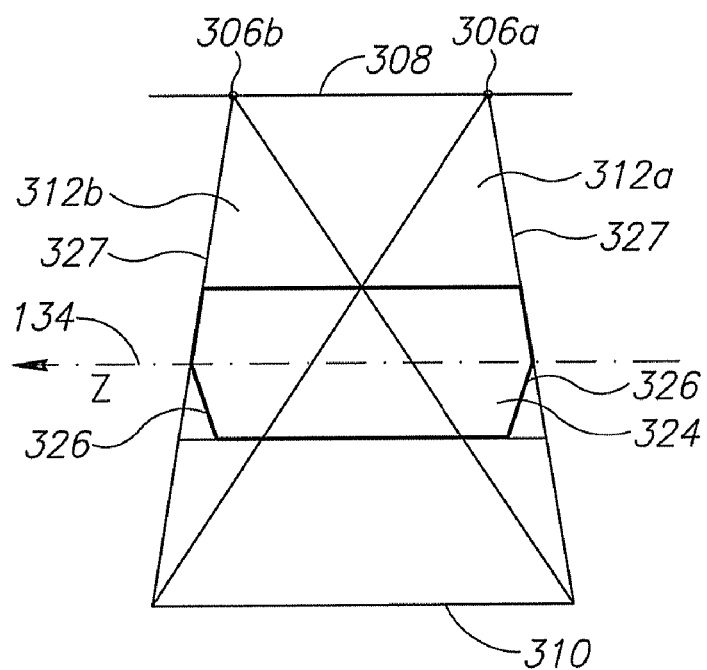
FIGS. 3B and 3C are schematic illustrations of axially displaced X-ray sources and the resulting scan volume for the embodiment of FIG. 3A.
Figure 3C:
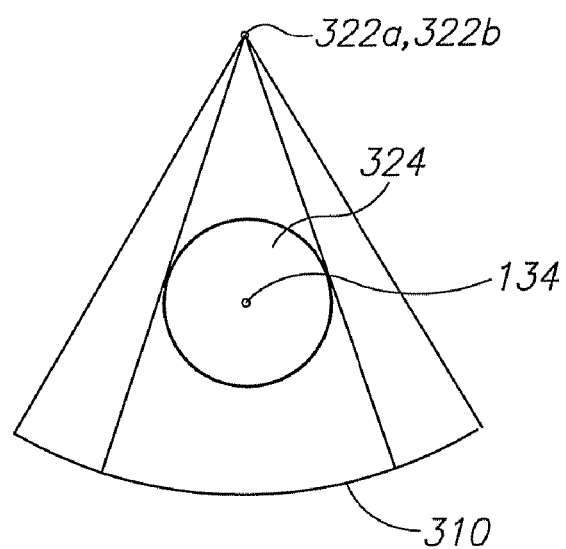

FIGS. 3A-3C illustrate a second embodiment of a CT scanner according to the invention. Here, scanner 300 is comprised of a rotor 302 that carries an X-ray source 304 that provides two X-ray beam emission points 306a and 306b for X-ray beams 312a and 312b. Emission points 306a and 306b are axially spaced along a line 308 on rotor 302 parallel to an axis of rotation 134. Emission points 306a and 306b may be provided by separate X-ray tubes or by two focal spots of single tube as in the '633 Patent Application and the '587 Patent referred to above; more than two beams spaced and arranged in any suitable or desired manner may optionally be provided as well.

A detector array 310 formed of columns and rows of detector elements 314 is mounted on rotor 302 in a position to intercept X-ray beams 312a and 312b after the beams pass through a subject on a support platform (not shown) like that of FIG. 2.

For imaging of small subjects, and particularly in cardiac imaging, however, use of cone beams can be advantageous. As shown in FIGS. 3B and 3C, which are a schematic cross-section and axial end view respectively, beams 312a and 312b emanating from focal points 306a and 306b combine to form a generally cylindrical VFOV 324 with slightly conical ends 326 along rotation axis 134.

Beams 312a and 312b are switched on and off, alternating rapidly. With properly spaced beams and a properly sized and oriented detector array 310, a cylindrical VFOV 324 is obtained that may be large enough to produce a three-dimensional image of good resolution of the entire heart without changing the axial position of the subject support platform.

This is advantageous because the cardiac cycle is characterized by periods of intensive movement (contraction) and alternating relatively quiescent periods. By initiating a CT scan at the beginning of a relatively quiescent period, a scan can be completed before the next contraction. This avoids the need for coordinating data from multiple scans and can reduce computational complexity.

As will be appreciated, if the VFOV 324 is not long enough axially for a particular application, the support platform may be advanced as necessary to obtain a scan volume of the desired length.

Apart from the foregoing, scanner 300 is generally like scanner 200, and is used in essentially the same manner as scanner 200. Further description is accordingly omitted in the interest of brevity.

Referring again to FIG. 2, scanner 200 is constructed and controlled for use in a preliminary positioning mode utilizing the dual beam X-ray source 204, and in a primary CT imaging mode that may utilize one or both of the beams generated by source 204.

In the positioning mode, a patient (not shown) is first placed using light markers or other means such that the VOI is generally covered by the scanner imaging field. X-ray cone beams 234a and 234b are emitted alternatingly, at respective emission angles such that the beams impinge on detector array 208 in the same area, and thus form images of overlapping regions as seen from offset viewpoints.

Several timing options are possible. In general, one or more stereo image frames may be taken, with beams 234a and 234b switched on and off for a duration and repetition rate compatible with the subject to be imaged. As an example, for cardiac imaging, a number of repetitions in the range of 15-30 per second would be suitable. Using a repetition rate of 25 stereo frames per second, each cycle would have 40-millisecond duration. Beam 234a would be switched on for 5 milliseconds, then beam 234b would be switched on for 5 milliseconds. The remaining 30 milliseconds of the repetition period would be inactive. Higher or lower imaging rates may be applied.

Alternatively, stereo images may be produced one at a time at the operator's request. In such cases, each source will be activated once to generate the one stereo image For cardiac imaging, it is advantageous to synchronize the generation of the stereo image data with the relatively quiescent portions of the cardiac cycle between contraction. To do this, an ECG output signal may be used to trigger successive stereo imaging repetition cycles: at the beginning of a quiescent period, beam 234a may be turned on for 5 milliseconds followed by a 5 millisecond on time for beam 234b. Beams 234a and 234b would then remain inactive until triggered by the ECG signal indicating the beginning of the next quiescent period between contractions.

Data provided by detector array 208 is computer-processed using conventional techniques in the field of X-ray fluoroscopy to generate real time planar image data for each of beams 234a and 234b. According to the invention, positioning can be performed in three alternative ways: manually, semi-automatically with operator assistance, and fully automatically. For manual positioning, the two sets of image data are employed to create a composite stereo image for viewing by an operator. The operator uses the stereo image to manually position platform 222 relative to the VFOV of the scanner, as described below.

For stereo visualization, the computer generated planar stereo component images are arranged to be viewed separately by the left and right eyes of an operator so that the two separate images are integrated by the operator's brain into a three-dimensional image. An offset of between about four degrees and ten degrees between the beams 234a and 234b, preferably between four and seven degrees, for example, about six degrees, yields good results. However, higher or lower offset may also be employed.

Various ways are known for presenting spaced image data to create a stereoscopic effect, and any suitable one may be employed. For example, the separate images may be viewed using a head mounted electro-optically switched viewer, e.g., of the kind shown in Roese et al. U.S. Pat. No. 4,214,267, the content of which is incorporated herein by reference. In such an arrangement, separate viewing windows are provided for each eye. The two images are displayed on a single monitor in alternating fashion, but the viewing windows are alternatingly blocked in synchronism with the alternating images so one image is viewable only by the left eye, and the other image is viewable only by the right eye.

Alternatively, separate monitors may be provided in a head-mounted viewer to display only one image for each eye.

Another option is the so-called "autostereo" display technology. As known to those skilled in the art, this is a conventional technology in which a single monitor is designed to display two images but in such a way that one image is visible only to the left eye, and the other image is visible only to the right eye. Several ways to implement this are known, and autostereo monitors are available commercially from several sources, e.g. Sharp Corporation.

Manual adjustment does not necessarily require viewing a stereo image and can optionally be done by bringing a feature of interest in the subject to predefined location in both images.

Figure 4:
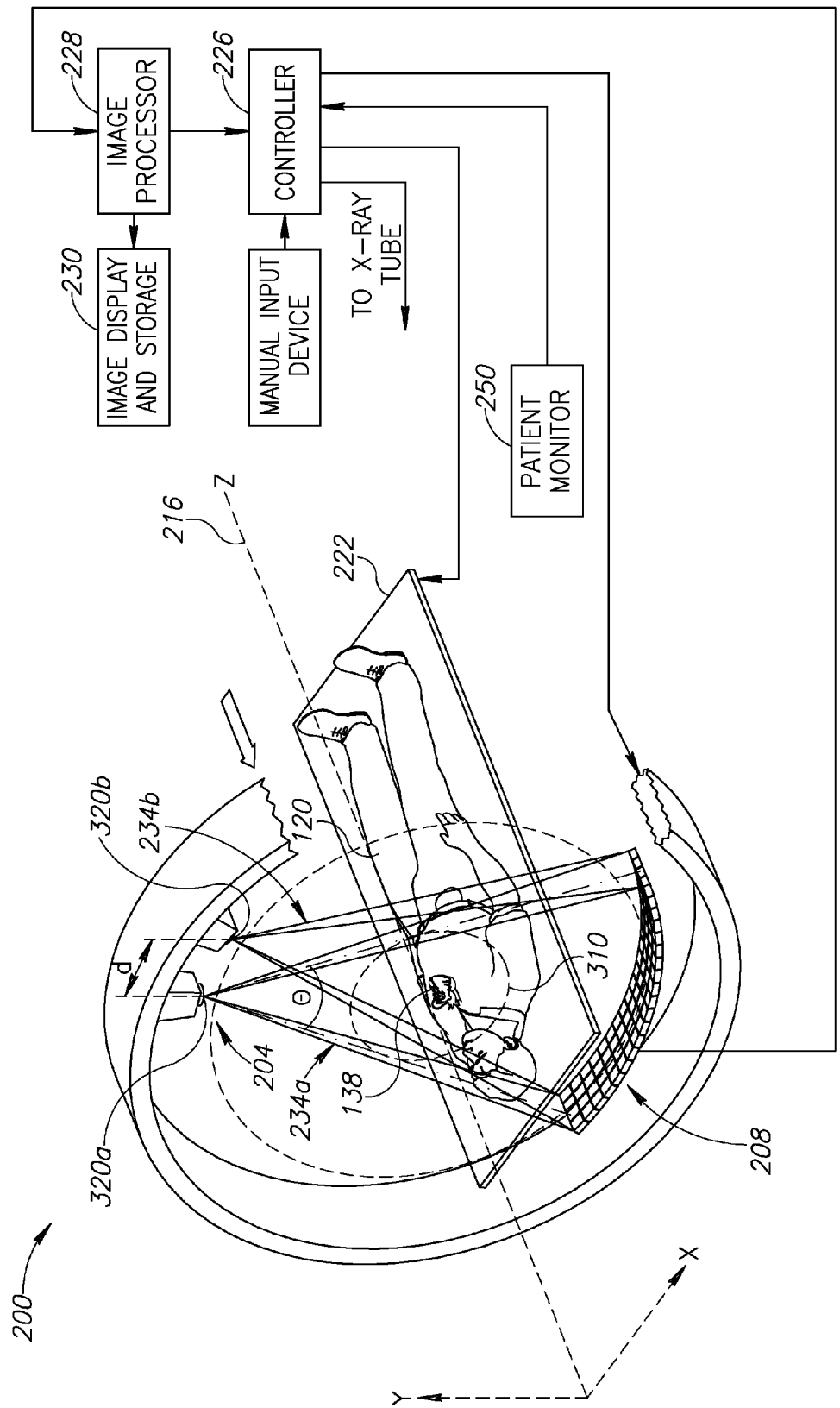
FIG. 4 is a pictorial perspective view showing the CT scanner of FIG. 2 being used to create a stereo-fluoroscopic positioning image.

Operation of scanner 200 in the positioning mode is illustrated in FIG. 4. Here, a patient platform 222 is shown positioned so that a patient 120 is within the composite field of view created by X-ray beams 234a and 234b (or a volumetric field of view resulting from spacing of X-ray emission points along the Z-axis, as in the embodiment of FIGS. 3A through 3B).

For purposes of explanation, it is assumed that the operator has initially positioned platform 222 with the patient's heart 138 offset along scanner Z-axis (axis of rotation) 216 from an X-Y plane of symmetry 310 of X-ray beams 234a and 234b and also offset from the Z axis of rotation in an X-Y plane perpendicular to the rotation axis.

As an optional preliminary setting, the operator can define the VOI, for example by selecting a clinical imaging option such as "Cardiac Scan" from among several available control settings using manual input device 232. This may be used to provide assistance to the operator in manual and semi-automatic positioning modes by superimposing a graphic overlay on the subject stereo images that shows the center and borders of the designated field of view for the CT scan.

As will be appreciated, for different clinical applications, the scanner FOV may optimally have a different diameter and/or length along Z axis, and, in a manner which will be readily apparent to those skilled in the art, controller 226 will be programmed to generate an appropriately shaped and positioned graphic overlay.

The reference guide may be in any desired form, for example, a representation of the scanner VFOV, or an X-Y plane containing the emission points 320a and 320b of beams 234a and 234b and Z-axis 216, or even a schematic representation of the scanner itself, similar to FIG. 2 herein. Numerous display-programming techniques are known to those skilled in the art by which the desired reference guide may be generated and displayed.

As an alternative to definition of the VOI size by preselection, controller 226 may be programmed to permit the operator to use input device 232 to mark on the acquired images, the general boundaries (width and length) of the VOI to be scanned.

Pre-defining the VOI in either of the above indicated ways takes account of the fact that for a given scanner configuration, a certain physical volume (VFOV) will be imaged with the best resolution and allows more accurate centering of the VOI in the VFOV.

As previously mentioned, for clinical applications such as cardiac imaging, it may be advantageous to initiate a positioning operation at a desired time. For this purpose, a patient may be connected to one or more monitoring units indicated schematically at 250 in FIG. 4. The monitoring units may include an ECG, or a breathing monitor or both. A patient's cardiac cycle heartbeat or breathing may be monitored, from the raw ECG data obtained may be used to trigger positioning image acquisition at a desired phase of a patient's cardiac or breathing cycle. Optionally, a dedicated breathing monitor may be provided; often, a breath monitor is used during projection data acquisition in any event.

ECG and/or breath-monitoring data may also be used to identify the phase in the cardiac cycle at which the positioning images were taken and the information taken into consideration when centering the VOI. This can be advantageous since both heartbeat and breathing result in cyclical translational motion of the heart and expansion and contraction of the heart wall boundary. Controller 226 may be programmed to determine such positional variation in relation to the phases of the cardiac cycle, and any necessary positional correction can be made when calculating the optimal position for the VOI.

Optionally, the patient can be asked to hold his breath at a certain breathing phase; this is often done in conventional CT scanning during the projection image acquisition.

When a positioning scan is to be undertaken, beams 234a and 234b are rapidly switched on and off as described above so that both beams capture essentially the same phase of the heartbeat. The output of detector 208 is processed by image processor 228 to generate planar X-ray images formed by the two beams.

For manual positioning, an operator inspects the stereo image generated by image processor 228 from the output of detector array 208, for example, using one of the techniques described above.

Because the image of the heart appears to be three dimensional, the operator can readily see the offset of the heart from the optimum position in the X, Y, and Z directions, and can manually reposition platform 222 to align it with the superimposed reference guide by actuating X, Y, and Z drive motors (not shown) for platform 222.

For semi-automatic (user assisted) or fully automatic positioning, there is no need for real time fluoroscopic imaging. It is sufficient to acquire two single images, from X ray beams 234a and 234b. The initial location and orientation of the VOI is first determined from the single images. From this information, platform 222 is automatically moved from its initial position to the desired position.

Determination of the initial location and orientation can be done, for example, by identifying matching portions of the stereo image components, such as the edge or outline of the heart. For semi-automatic (user assisted) positioning, by way of example, controller 226 may be programmed to display the stereo component images separately, and to permit the operator to mark the matching boundaries on the two images.

For completely automatic positioning operation, any suitable known image-processing algorithm such as pattern matching and stereo correspondence algorithms can be used to locate corresponding parts of the stereo component images. As a simple example, conventional image processing methods may be used to determine the contour of the heart shadow on the detector for each source. From this, the lateral shift between the images may be determined. Since the distances from the x-ray emission points to the detector are known, geometrical calculation of the average height of the heart, and therefore determination of its location relative to the scanner coordinate system will be entirely straightforward and readily implemented by a person skilled in the art.

It might also be noted that optionally, the geometric calculation can include compensation for minor errors likely to result from visual matching of corresponding "edges" of a 3D image for two viewing angles. To appreciate the nature of the problem, for the case of a simple 3D object such as a sphere, in projections generated from two different angles, the edges in the images will be formed by a slightly different physical location on the sphere, corresponding each to the location tangent to the ray from the source. If these apparent corresponding edges are matched when performing the geometric calculations, an error will be introduced. By using the radius of curvature (in the case of a sphere), or an estimated radius in the case of a heart or other organ, compensation for this error can be provided.

After the initial location of the ROI is determined, the controller positions platform 222 in the horizontal plane automatically, both laterally and along the Z axis. For automatic vertical positioning, a depth calculation can be performed using any conventional triangulation method to compute the position of the heart boundary relative, for example, to the emanation point of one or both of the X-ray beams. Known computer implemented triangulation methods such as epipolar constrained triangulation can readily be employed for this purpose by persons or ordinary skill in the art in light of the description herein.

It should be appreciated that the projection data from the displaced sources created in a single projection imaging contains all the necessary information for fully automated positioning, and display of the stereo image would not be essential in the event of fully automatic platform positioning. It should also be appreciated that conventional procedures can be followed for positioning in the horizontal plane, while a triangulation process as described above, either in an operator-assisted mode, or a fully automatic mode could be used for positioning in the vertical direction.

It should also be appreciated that it is even possible to employ a physical arrangement as shown in FIG. 1 having a single X-ray emission point to produce the stereo image data. This may be accomplished by obtaining two images from X-rays emitted from the single X-ray emission point. A first image is obtained with the subject platform at a first location, and a second image is obtained after the subject platform has been moved a small distance (e.g., 50 mm.) in a direction transverse to the beam direction such that there is good overlap between the resulting images.

After positioning of platform 222 so that the subject's heart 138 is properly positioned, in the scan volume, the CT scan proceeds, using one or both X-ray emission points 206a, 206b (FIGS. 2 and 4) or 306a, 306b (see FIGS. 3B and 3C).

Figure 5:
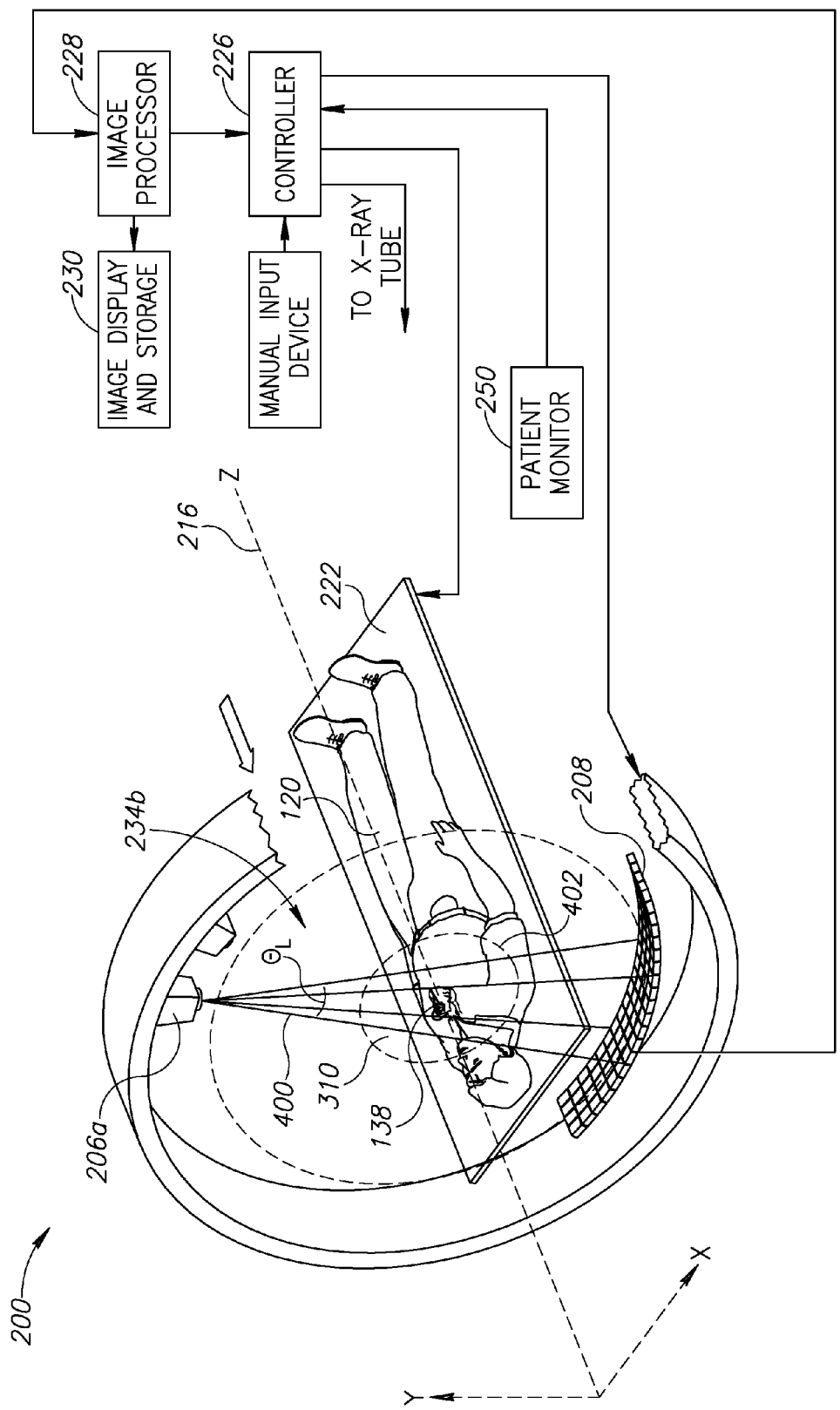
FIG. 5 is a pictorial perspective view showing the CT-of FIG. 2 being used to perform a CT-scan within a limited field of view.

Referring to FIG. 5, platform 222 is shown positioned so that the patient's heart 138 is centered in the scanner FOV and along the scanner Z-axis 216. X-ray source 204 or source 304 (see FIG. 3A) is activated, and a scan is performed at a single axial position, using one or both X-ray beams or at a succession of axial positions as needed to obtain the desired scan volume.

As an incidental benefit of the invention, when the scanner is to be used only for cardiac imaging or other applications requiring only a relatively small FOV, the overall size of the scanner can be reduced. Such reduced-size scanners can be less expensive than conventional general-purpose CT scanners, and consequently, might be affordable by smaller medical offices, and not just hospitals and large radiology centers, or by other smaller facilities.

The invention has been described with reference to embodiments thereof that are provided by way of example and are not intended to limit the scope of the invention. Application of the invention to cardiac imaging is described as a non-limiting example, but it will be understood that the invention is also applicable to alignment of other organs or other subjects for CT imaging. The described embodiments comprise different features, not all of which are required in all embodiments of the invention. Some embodiments of the invention utilize only some of the features or possible combinations of the features. Variations of embodiments of the described invention and embodiments of the invention comprising different combinations of features than those noted in the described embodiments will occur to persons of the art. The invention is intended to encompass all such variations and other embodiments, and scope of the invention is intended to extend fully to the limit permitted by the following claims.

The invention claimed is:

1. A CT scanner for imaging a region of interest of a subject, the CT scanner comprising:
    a source of X-ray beams,
        wherein the source is adapted to provide at least one beam for acquiring a CT image of the subject, wherein X-rays emanate from a plurality of emission points that are spaced transversely to a direction of rotation of the X-ray beams around the subject on a line parallel to an axis of rotation of the X-ray beams;
    a support to support the subject; and
    a controller to control the X-ray source to illuminate the region of interest with X-rays to acquire stereo image data for the region of interest and wherein the controller is to further control the position of the support responsive to the stereo image data.

2. A CT scanner according to claim 1, comprising:
    at least one detector array to receive X-rays provided by the X-ray source and to define with the X-rays a field of view of the CT scanner.

3. A CT scanner according to claim 2, wherein the controller is to control the support to center the region of interest in the field of view.

4. A CT scanner according to claim 1, wherein the X-rays emanate from a plurality of X-ray focal spots located in a single X-ray tube.

5. A CT scanner according to claim 1, wherein the plurality of X-ray beams emanate from separate X-ray tubes.

6. A CT scanner according to claim 1, wherein the stereo image data represents a real time fluoroscopic stereoscopic image.

7. A CT scanner according to claim 1, wherein the stereo image data represents two separate images, and wherein the controller is operative to apply an image processing algorithm to the separate images to control the position of the support.

8. A CT scanner according to claim 1, wherein the controller is operative to provide visual data to an operator for use by the operator in controlling the position of the support in one or more dimensions.

9. A CT scanner according to claim 1, wherein the controller is operative to control the position of the support in a fully automatic mode, or in a semi-automatic mode, responsive to input data from an operator.

10. A CT scanner according to claim 1, wherein the controller is operative to control the position of the support in a direction substantially parallel to the X-ray beams.

11. A method of operating a CT scanner to acquire a CT image of a region of interest of a subject,
    wherein the CT scanner is operable to generate X-rays from a source having at least one emission point and having a detector array that cooperates with the X-ray source to define a field of view for the CT scanner,
    the method comprising:
    illuminating a region of the subject encompassing the region of interest using X-rays emitted from the X-ray source;
    generating stereo image data for at least part of the illuminated region responsive to an output from the detector array;
    positioning the region of interest at a desired location relative to the CT scanner in response to the stereo image data; and
    generating a CT image of the region of interest positioned at the desired location.

12. The method according to claim 11, wherein the desired location at which the region of interest is positioned is substantially centered along a rotational axis of the CT scanner.

13. The method according to claim 11, wherein the region of interest is a heart of the subject, and wherein the stereo image data is generated responsive to a selected phase of a cardiac cycle of the subject or a selected breath phase of the subject.

14. The method according to claim 13, wherein the phase of the cardiac cycle is determined from an ECG signal.

15. The method according to claim 13, wherein the breath phase of the patient is determined from a breath monitor signal.

16. The method according to claim 11, wherein the stereo image data is generated by alternatingly illuminating the region of the subject encompassing the region of interest using X-rays emitted from two emission points which are switched on an off during multiple repetition cycles.

17. The method according to claim 11, wherein the region of interest is a heart of the subject, and wherein the method further comprises:
    using an ECG signal to identify a phase of the cardiac cycle at which the stereo image data were generated; and
    generating the CT image using the identified phase of the cardiac cycle for timing.

18. The method according to claim 11, wherein the region of interest is a heart of the subject, and the method further comprises:
    selecting a breath phase at which the stereo image data will be generated using a signal from an ECG or from a breath monitor; and
    generating the CT image of the region of interest at the same breath phase for which the stereo image data were generated.

19. The method according to claim 11, wherein generating the stereo image data comprises obtaining first and second images from X-rays emitted from a single X-ray emission point, the first image being obtained with the subject platform at a first location, and the second image being obtained after the subject platform has been moved a small distance in a direction transverse to the beam direction such that the resulting first and second images overlap.

20. The method according to claim 11, wherein generating the stereo image data comprises illuminating the region of the subject encompassing the region of interest with multiple repetition cycles of X-rays from a first X-ray emission point and a second X-ray emission point, each repetition cycle being comprised of a first period during which X-rays are emitted only from the first emission point and a second period of approximately the same duration as the first period during which X-rays are emitted only from the second emission point, wherein the combined duration of the first and second periods is less than the total duration of the repetition period.

21. The method according to claim 20, wherein the region of interest is a heart of the subject, and wherein the repetition period is based on a cardiac cycle as indicated by an ECG output signal.

22. A CT scanner for imaging a region of interest of a subject, the CT scanner comprising:
    an X-ray source to provide X-rays from multiple emission points;
    a platform for supporting the subject;
    a detector array positioned to intercept X-rays emitted by the X-ray source; and
    a controller to control the X-ray source to generate X-rays from two emission points to illuminate the subject, wherein the controller is responsive to an output from the detector array when illuminated by X-rays from the two emission points to generate stereo image data for the subject;

wherein the controller is responsive to the stereo image data to position the platform at a desired location for acquiring a CT image of the region of interest, wherein the controller is to illuminate the region of interest with X-rays from the X-ray source, and responsive to an output of the detector array when operated in the scanning mode to generate a CT image of the region of interest.

23. A CT scanner according to claim 22, wherein the two X-ray emission points are first and second X-ray focal spots at spaced locations in a single X-ray tube or in separate X-ray tubes.

24. A CT scanner according to claim 22, wherein the two X-ray emission points are spaced in a direction of rotation of the X-ray beams around the subject, or are spaced transversely to a direction of rotation of the X-ray beams around the subject on a line parallel to an axis of rotation of the X-ray beams.

25. A CT scanner according to claim 22, wherein the controller is to provide visual data to an operator for use by the operator in controlling the position of the platform in one or more dimensions.

26. A CT scanner according to claim 22, wherein the controller is to control the position of the platform in a fully automatic mode, or in a semi-automatic mode, responsive to input data from an operator.

27. A CT scanner according to claim 22, wherein the X-rays from the two emanation points are switched on an off repeatedly in alternation while the stereo image data is being generated.

* * * * *